US00PP32562P2

(12) United States Plant Patent
Smit

(10) Patent No.: US PP32,562 P2
(45) Date of Patent: Dec. 1, 2020

(54) ***PEPEROMIA* PLANT NAMED 'EC-PEPE-1905'**

(50) Latin Name: *Peperomia caperata*
Varietal Denomination: EC-PEPE-1905

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 16/873,172

(22) Filed: Feb. 18, 2020

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct cultivar of *Peperomia* plant named 'EC-PEPE-1905' is disclosed, characterized by a very compact habit, and small foliage with a distinct light grey color. The new variety is a *Peperomia*, typically used as an ornamental plant.

3 Drawing Sheets

Latin name of the genus and species: *Peperomia caperata.*

Variety denomination: 'EC-PEPE-1905'.

BACKGROUND OF THE INVENTION

The new cultivar is a product of a planned breeding program. The new variety was selected as a seedling resulting from the crossing of two unnamed, unpatented varieties of *Peperomia caperata*. The crossing was made by the inventor, Obed J. Smit in 2013. 'EC-PEPE-1905' was selected by the inventor in 2016 at a commercial greenhouse in Sappemeer, the Netherlands.

Asexual reproduction of the new cultivar 'EC-PEPE-1905' by leaf cuttings was first performed in Sappemeer, the Netherlands at a commercial greenhouse in March 2016 and has shown that the unique features of this cultivar are stable and reproduced true to type through successive generations.

SUMMARY OF THE INVENTION

The cultivar 'EC-PEPE-1905' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-1905' These characteristics in combination distinguish 'EC-PEPE-1905' as a new and distinct *Peperomia* cultivar:

1. Very compact growth habit.
2. Small leaves.
3. Distinct light grey leaf color.

PARENT COMPARISON

Plants of the new cultivar 'EC-PEPE-1905' are similar to plants of the female parent in most horticultural characteristics, however, plants of the new cultivar 'EC-PEPE-1905' differ from in the following characteristics:

1. The new variety has smaller leaves than the seed parent.
2. The new variety has a more compact habit than the seed parent.
3. The leaf upper side of the new variety is light grey, while the leaf upper side of the seed parent is grey-green.

Plants of the new cultivar 'EC-PEPE-1905' are similar to plants of the male parent in most horticultural characteristics, however, plants of the new cultivar 'EC-PEPE-1905' differ in the following characteristics:

1. The new variety has a more compact habit than the pollen parent.
2. The leaf upper side of the new variety is light grey, while the leaf upper side of the pollen parent is grey-green.
3. The new variety has round leaves, while the pollen parent has more pointed leaves.

COMMERCIAL COMPARISON

Plants of the new cultivar 'EC-PEPE-1905' are similar to plants of the commercial variety *Peperomia caperata* 'Eden Rosso', U.S. Plant Pat. No. 24,379. However, plants of the new cultivar differ in the following characteristics:

1. Leaf upper side of the new variety light grey, while the leaf upper side of this comparator is dark green.
2. Leaf under side of the new variety is light green, while leaf under side of this comparator is red.
3. Leaves of the new variety are rounder with a less elongated acute tip.

Plants of the new cultivar 'EC-PEPE-1905' are similar to plants of the variety *Peperomia* 'Napoli Nights', U.S. Plant Pat. No. 29,416. However, plants of the new cultivar differ in the following characteristics:

1. The new variety has smaller leaves than this comparator.
2. The new variety has a more compact habit than this comparator.

3. Leaf under side of the new variety is light green, while leaf under side of this comparator is orange-red.

BRIEF DESCRIPTION OF THE PHOTOGRAPHS

The accompanying photograph in FIG. 1 illustrates in full color a typical blooming plant of 'EC-PEPE-1905' grown in a greenhouse. The plant approximately 25 weeks of age.

Figure 1:
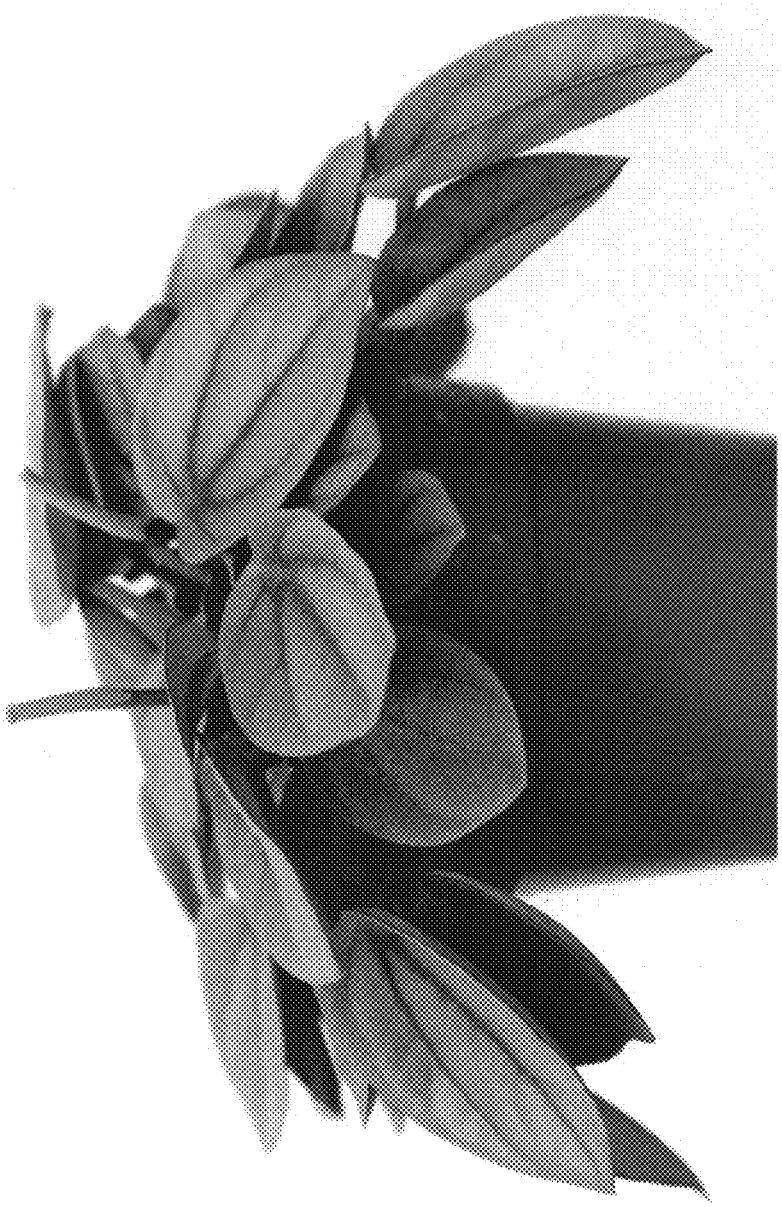
Figure 2:
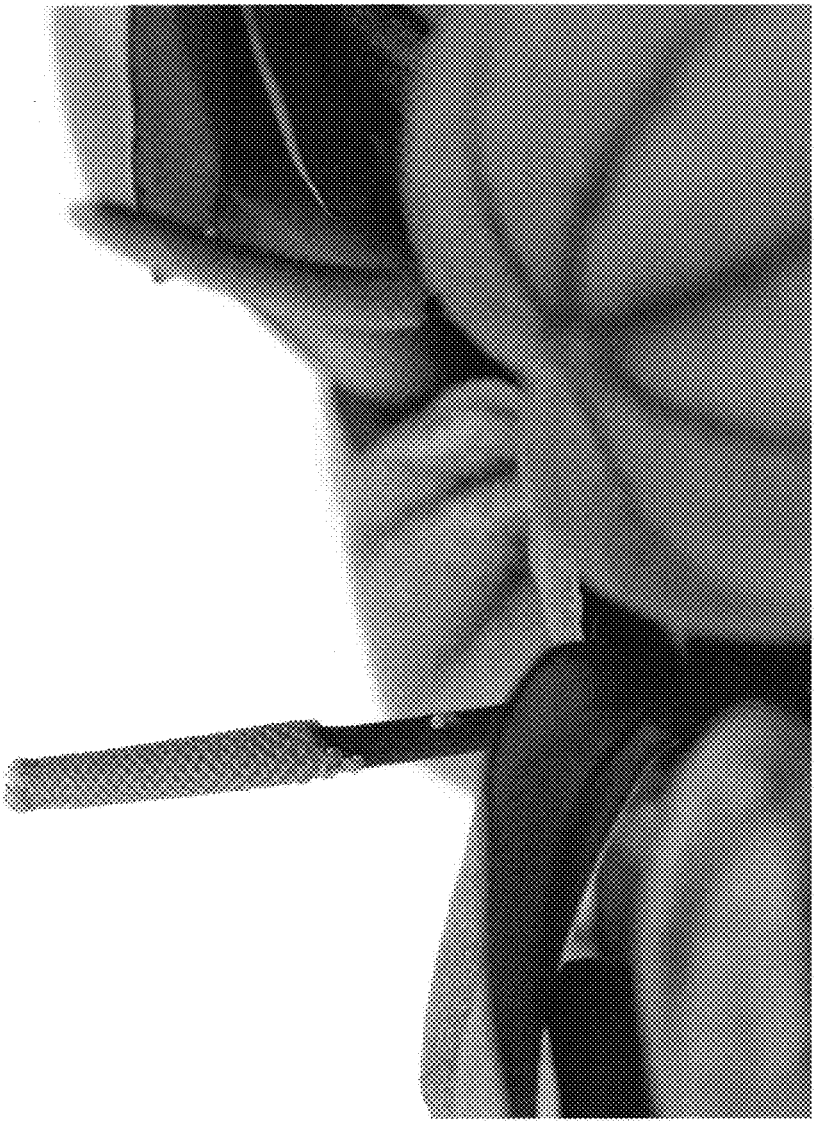
FIG. 2 illustrates a close-up view of the floral spike.
Figure 3:
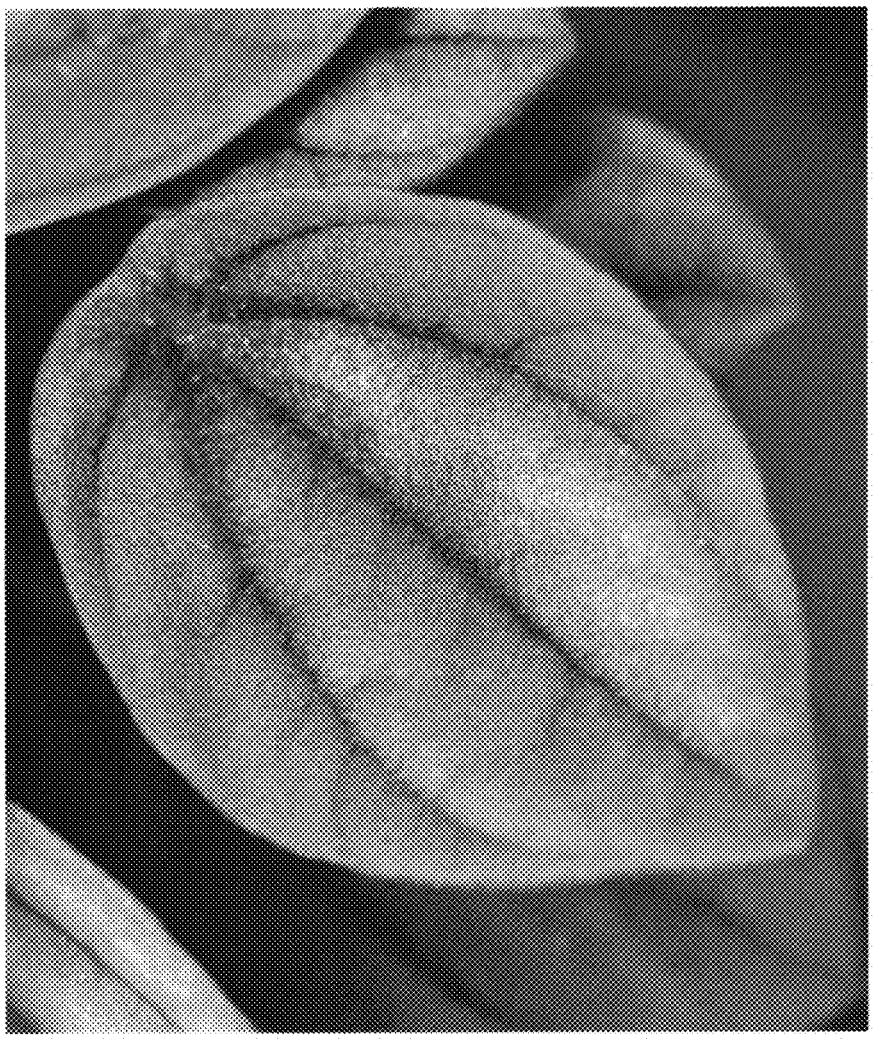
FIG. 3 illustrates a close-up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-1905' plants at 25 weeks of age, grown in a greenhouse in Sappemeer, the Netherlands during August of 2019. The growing temperature ranged from 17° C. to 20° C. at night to 19° C. to 21° C. during the day. Measurements and numerical values represent averages of typical flowering types.

Botanical classification: *Peperomia caperata* 'EC-PEPE-1905'.

PROPAGATION

Time to initiate roots: About 21 days at approximately 20° C. in Summer.

Time to produce rooted cutting: About 25 days at 20° C. in Summer.

Description of roots: Herbaceous, fine, moderately dense, freely branching. White in color, not accurately measured with R.H.S. chart.

PLANT

Plant type: Perennial potted plant.

Plant shape: Flattened with inflorescences growing in between the foliage.

Growth habit: Rosettes of leaves, will eventually form very short thick stems.

Plant spread: Approximately 11.2 cm.

Height: 4.1 cm to top of foliar plane; 4.8 cm to top of floral plane.

Growth rate: Low.

Plant vigor: Low to moderate.

Age of plant described: Approximately 25 weeks from a rooted cutting.

Branching habit: Leaves in rosettes, forming very short thick main stems, branching into lateral rosettes of leaves.

Pinching: Not required.

Number of primary (main) branches per plant: Average 7.

Number of secondary (lateral) branches per plant: Average 14.

Lateral stems:

*Length*.—Average 6 cm.

*Diameter*.—Average 4 cm.

Internode length: Average Less than 0.1 cm.

General appearance and shape: Succulent, thick and rounded.

Luster: Slightly glossy.

Aspect/angle from vertical: Average 20°.

Strength: Moderately strong.

Color:

*Developing*.—RHS Greyed-Red 178A.

*Mature*.—RHS Greyed-Red 178A.

*At internodes*.—RHS Greyed-Red 178A.

Pubescence: None.

FOLIAGE

Leaf:

*Arrangement*.—Alternate, single.

*Quantity*.—Average 10.

*Average length*.—3 cm.

*Average width*.—2.3 cm.

*Shape of blade*.—Ovate, perfoliate.

*Apex*.—Broad acute.

*Base*.—Truncate, lobes connected thus forming perfoliate leaf.

*Margin*.—Entire.

*Aspect*.—Very slightly concave.

*Texture of top surface*.—Glabrous, smooth, moderately leathery.

*Texture of bottom surface*.—Glabrous, smooth, moderately leathery.

*Pubescence*.—None.

*Luster, upper side*.—Moderately glossy.

*Luster, under side*.—Matte.

*Color*.—Young foliage upper side: RHS Greyed-Green N189C, veined N189A. Young foliage under side: RHS Yellow-Green 148D, veined 147B. Mature foliage upper side: RHS Greyed-Green 189C, overlaid Black 202D. Mature foliage under side: RHS Yellow-Green 148D.

*Venation*.—Type: Parallel, moderately furrowed. Venation color upper side: RHS Greyed-Green N189A, but considerably darker. Venation color under side: RHS Greyed-Green 191A and 191B.

*Petiole*.—Average Length: 3.1 cm. Diameter: 0.2 cm. Texture: Glabrous, smooth. Strength: Low. Luster: Both sides moderately glossy. Color, upper side: RHS Greyed-Red 181A, moderately finely striped Yellow-Green 147D and lighter; less densely towards distal end. Color, under side: RHS Greyed-Red 181A, moderately finely striped Yellow-Green 147D and lighter; less densely towards distal end.

FLOWER

Inflorescence:

*Arrangement*.—Axillary spike.

*Type and form*.—Spike.

*Height*.—Average 2 cm (excluding peduncle).

*Diameter*.—Average 2 mm, inflorescences occasionally cleft at the top (fascinating), average diameter when fascinating: 2.0 mm.

*Flowers per iflorescence*.—Average 600 individual flowers per spike.

*Flowers per plant*.—Average 300.

*Flower buds per plant*.—Average 300.

*Flowers and buds per plant*.—Average 600.

*Natural flowering season*.—Late Winter to late Spring.

Bud:

*Length*.—0.3 mm.

*Diameter*.—0.3 mm.

*Shape*.—Flattened.
*Texture*.—Glabrous, smooth.
*Luster*.—Slightly glossy.
*Color*.—Near RHS Yellow-Green 147C.

Flower:
*Type and form*.—Individual flowers are minute and have no petals or sepals but consist of 2 stamens and a single pistil.
*Aspect*.—Outward.
*Habit*.—Very free-flowering.
*Fragrance*.—None.
*Shape*.—Rotate, consisting of 2 stamens and one pistil only; no petals and sepals present.
*Height*.—Average 0.5 mm.
*Diameter*.—Average 0.5 mm.
*Length*.—Average 0.5 mm.
*Longevity on plant*.—Average one month.
*Persistence*.—Self-cleaning.

Petals: None.
Petaloids: None.
Sepals: None.

Peduncle:
*Length*.—Average 3.4 cm.
*Diameter*.—Average 2 mm.
*Angle*.—25°.
*Strength*.—Moderately weak.
*Texture*.—Glabrous, smooth.
*Luster*.—Slightly glossy.
*Color*.—RHS Greyed-Red 178A.

Pedicel: None.

Floral bracts: Below each individual flower a single bract is present, shaped orbicular, average length and width: 0.4 mm, colored RHS Yellow-Green 147B.

REPRODUCTIVE ORGANS

Stamens:
*Number*.—Average 2.
*Filament length*.—Average 0.1 mm.
*Filament color*.—Near RHS Yellow-Green 144B to 144C.

Anthers:
*Shape*.—Kidney.
*Length*.—Average 0.2 mm.
*Width*.—Average 0.2 cm.
*Color*.—Near RHS Yellow-Green 144B to 144C.
*Pollen*.—None detected.

Pistil:
*Number*.—Average 1.
*Length*.—Average 0.2 mm.

Stigma:
*Shape*.—Flattened, circular.
*Length*.—Average 0.2 mm.
*Diameter*.—Average 0.2 mm.
*Color*.—Near RHS Yellow-Green 143B or C.
*Style*.—No style visible, stigma sessile.
*Ovary color*.—Near RHS Yellow-Green 143B or C.

OTHER CHARACTERISTICS

Seeds and fruits: None observed to date.

Disease/pest resistance: No increased nor decreased resistance to normal diseases and pests of *Peperomia* has been observed.

Temperature tolerance: Tolerates temperatures up to 40° C., hardy to at least USDA zone 10. High wind tolerance.

What is claimed is:

1. A new and distinct cultivar of *Peperomia* plant named 'EC-PEPE-1905' as herein illustrated and described.

* * * * *